US012793303B2

(12) United States Patent
Eichner

(10) Patent No.: US 12,793,303 B2
(45) Date of Patent: Nov. 10, 2026

(54) GENERATION OF CEPHALOMETRIC X-RAY IMAGES BASED ON PANORAMIC IMAGING DATA

(71) Applicant: ZETTA25 AG, Zurich (CH)

(72) Inventor: Stefan Eichner, Heidelberg (DE)

(73) Assignee: ZETTA25 AG, Zurich (CH)

( * ) Notice: Subject to any disclaimer, the term of this patent is extended or adjusted under 35 U.S.C. 154(b) by 99 days.

(21) Appl. No.: 19/025,458

(22) Filed: Jan. 16, 2025

(65) Prior Publication Data

US 2026/0203981 A1 Jul. 16, 2026

(51) Int. Cl.

| | |
|---|---|
| ***A61B 6/51*** | (2024.01) |
| ***A61B 6/00*** | (2006.01) |
| ***A61B 6/06*** | (2006.01) |
| ***G06T 12/30*** | (2026.01) |
| ***G06T 17/20*** | (2006.01) |
| ***G06T 19/00*** | (2011.01) |

(52) U.S. Cl.

CPC ................ *G06T 12/30* (2026.01); *A61B 6/06* (2013.01); *A61B 6/51* (2024.01); *A61B 6/5205* (2013.01); *G06T 17/20* (2013.01); *G06T 19/00* (2013.01); *G06T 2210/41* (2013.01)

(58) Field of Classification Search

CPC ......... G06T 12/30; G06T 17/20; G06T 19/00; G06T 2210/41; A61B 6/06; A61B 6/51; A61B 6/5205

See application file for complete search history.

(56) References Cited

U.S. PATENT DOCUMENTS

| | | | |
|---|---|---|---|
| 2009/0232274 A1 | 9/2009 | Spartiotis et al. | |
| 2018/0174367 A1* | 6/2018 | Marom | G06T 19/006 |
| 2022/0031264 A1 | 2/2022 | Vlachomitrou et al. | |

FOREIGN PATENT DOCUMENTS

WO 2024110521 5/2024

OTHER PUBLICATIONS

"European Application Serial No. 26150632.3, Extended European Search Report mailed May 27, 2026", 4 pgs.

* cited by examiner

*Primary Examiner* — Uzma Alam
*Assistant Examiner* — Mamadou Faye
(74) *Attorney, Agent, or Firm* — SCHWEGMAN LUNDBERG & WOESSNER, P.A.

(57) ABSTRACT

Various aspects of systems, methods, and related aspects to generate cephalometric (CEPH) x-ray images based on panoramic image data from an extra-oral x-ray system are described. One example method of generating a computed CEPH image includes obtaining panoramic image data produced from a panoramic x-ray scan; generating a representation of the panoramic image data in a defined three-dimensional space; determining a geometry of a cephalometric view in the defined three-dimensional space; modeling simulated x-rays in the geometry of the cephalometric view to identify portions of the panoramic image data to be used in the computed cephalometric image; and outputting the computed cephalometric image.

20 Claims, 10 Drawing Sheets

GENERATION OF CEPHALOMETRIC X-RAY IMAGES BASED ON PANORAMIC IMAGING DATA

BACKGROUND

A cephalogram (CEPH) x-ray, also known as a cephalometric radiograph, is often used for diagnostic tasks and dental state evaluation by dentists, orthodontists, and other clinicians. Cephalograms are used, for example, to determine relevant positions in the patient's jaw during the planning, implementation, and follow-up of orthodontic and dental treatments. In some settings, a dedicated device called a CEPH arm may be added as an extension to an extra-oral X-ray system to capture a cephalometric projection and produce a cephalometric image (a "CEPH image").

For example, a CEPH arm may be added to panoramic radiography (orthopantomography) x-ray machines such as an extraoral device that is capable of capturing panoramic (PAN) views only or a combined extraoral device capable of capturing PAN and 3D scans. The positioning and exposure procedure used for capturing a CEPH view is different than the positioning and exposure procedure used for PAN views. The focus-detector distance for a CEPH x-ray is approximately 1.5 to 2 meters between source and detector, and a CEPH image is commonly produced using linear scan or one-shot technology. In addition to the significant cost of the additional equipment, the use of a CEPH arm will increase the required installation space of the x-ray machines, require additional adjustment and calibration, and require specialized involvement from service and technician personnel when a machine is installed or serviced.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
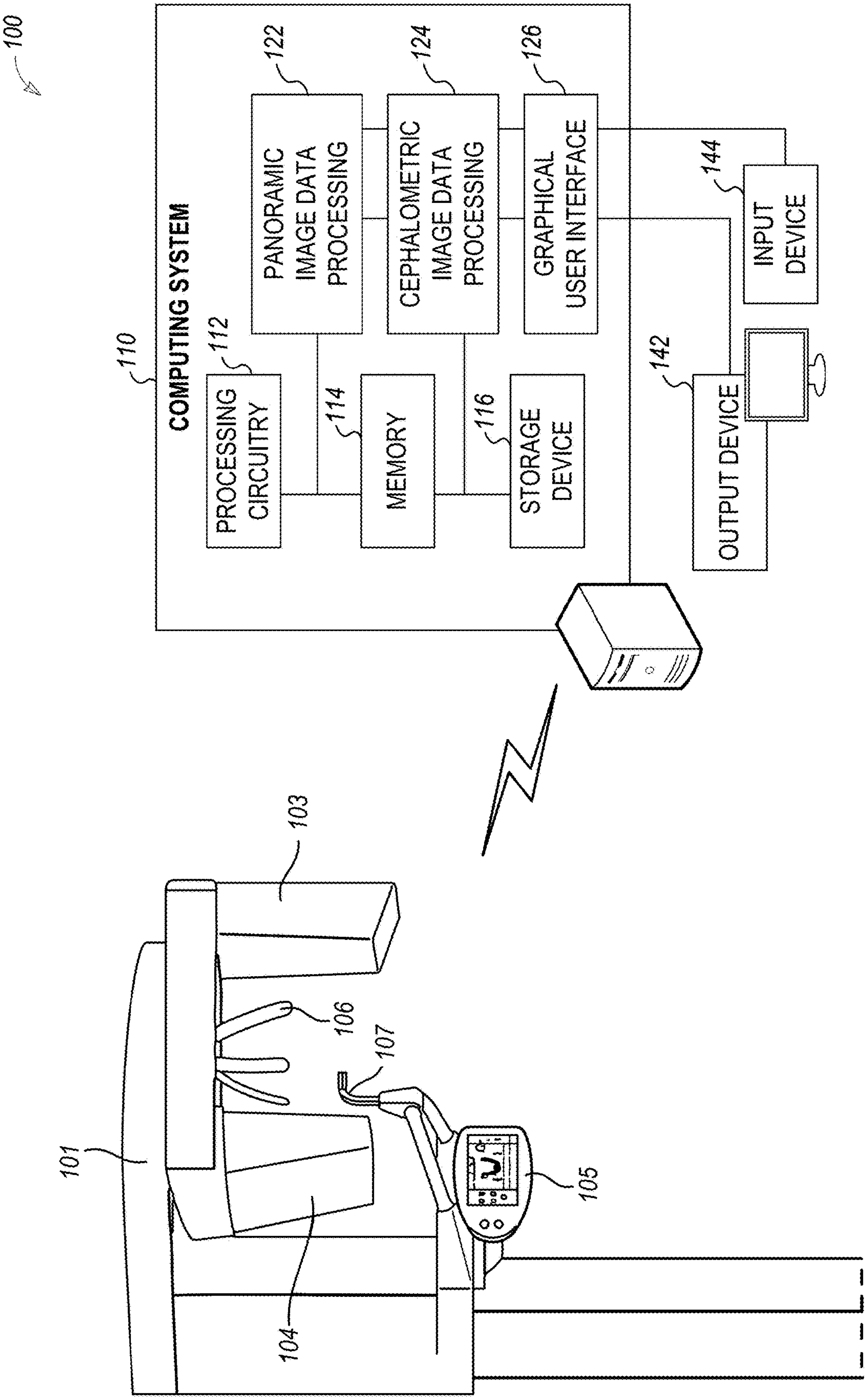
FIG. 1 depicts a computerized extraoral x-ray system, according to an example.

The following is directed to improvements to image processing technologies to generate a computed CEPH image from panoramic x-ray image data, without the use of specialized equipment such as a CEPH arm, dedicated CEPH x-ray sensors, or mechanisms that reposition a sensor to capture the CEPH image. Specifically, the following approaches can generate a computed CEPH image, also referred to herein as a calculated, synthetic, simulated, or artificial CEPH image, based on imaging data captured for a two-dimensional (2D) panoramic x-ray scan (e.g., an orthopantomography frontal radiograph). With the following approaches, 2D CEPH views may be produced from a full-frame panoramic (FFPAN) scan, such as from imaging data captured by a 2D or 2D/3D panoramic x-ray machine that also creates orthopantomogram images from the FFPAN imaging data. To create an FFPAN-based orthopantomogram image, over 4000 individual x-ray images are captured from different angular positions of the patient's jaw. The pixel resolution of a FFPAN sensor corresponds to the resolution typically used in a dedicated CEPH sensor and is significantly higher than that of a 3D (e.g., CBCT) sensor.

The approaches herein include a method for creating a 2D CEPH view based on the use of reconstructed FFPAN image data from a panoramic image represented in a 3D space. Individual x-ray projection images in FFPAN-based systems are available after a full scan of a patient and are used for the reconstruction of an FFPAN-based panoramic image, and the reconstructed panoramic image is then used for the reconstruction of a computed CEPH image. This generation of CEPH views based on FFPAN image data, and specifically from image data captured from a CMOS digital x-ray sensor, eliminates requirements for additional CEPH equipment and calibration. This means that it is no longer necessary to expand existing extraoral PAN or PAN/3D devices with a separate CEPH arm extension or integrate a new mechanism to move a panoramic x-ray sensor into a CEPH position. The resulting costs of sensors, machine installation, servicing, and additional expenses due to calibration, positioning, additional acquisition/dose, and service complexity associated with a CEPH arm extension can be avoided.

The approaches herein thus enable the generation of a computed CEPH image directly based on 2D panoramic image data, allowing the generation of multiple types of calculated CEPH views, including but not limited to a perspective corresponding to a standardized lateral cephalometric radiograph (e.g., a side view of the patient's head, including the bones and soft tissues of the face and skull). Even if the quality of the calculated CEPH views generated from the FFPAN scan data is reduced in comparison to a scan from a dedicated CEPH sensor, the approaches herein enable generating the CEPH view without needing separate scan equipment. This enables generating CEPH views in a variety of dental and orthodontic evaluation settings without the need for modified or new equipment. Additionally, these approaches enable CEPH views to be generated based on already-existing panoramic views.

FIG. 1 depicts a computerized extraoral x-ray system 100. As shown in FIG. 1, the x-ray system 100 includes an x-ray device 101 for performing the patient imaging. Prior to the exposure, the patient's head is preferably positioned in a center of the x-ray device 101, such as with a bite block 107 and a head fixation 106. As discussed below, the x-ray device 101 includes an x-ray emitter array 103 and an x-ray detector 104 that rotate around the patient's head to obtain x-ray images from different angles. The x-ray device 101 may include an operator device 105 that includes a basic user interface or operator controls (e.g., touch screen, buttons, etc.), to activate and control various functions of the x-ray system 100.

As also shown in FIG. 1, the x-ray system 100 may operably connect the x-ray device 101 with a separate computing system 110 (one or a set of multiple computers) and a separate output device 142 such as a display device to visualize data sets. The computing system 110 can be connected to the x-ray device 101 via a local network (not shown) or alternatively via a wide area network (e.g., the Internet). The computing system 110 may be part of a cloud computing deployment. In other examples, functions of the computing system 110 may be integrated into the x-ray device 101. Thus, the data processing operations described herein may take place on the x-ray device 101, on the computing system 110, or in a connected computing resource in the cloud.

For example, the computing system 110 may execute various computer programs and manipulate data sets to create different visualizations and representations of images. In some examples, the computing system 110 may provide commands to control the x-ray device 101 via the input device 144 or via programmatic control. Alternatively, separate computers may be used for image processing and device control operations. The data sets generated herein may be presented to a clinician (e.g., physician, dentist, trained staff, etc.) for visualization, in particular for diagnostic purposes, by use of the output device 142 or a communication to another type of output device such as a printer, screen, etc.

Figure 3:
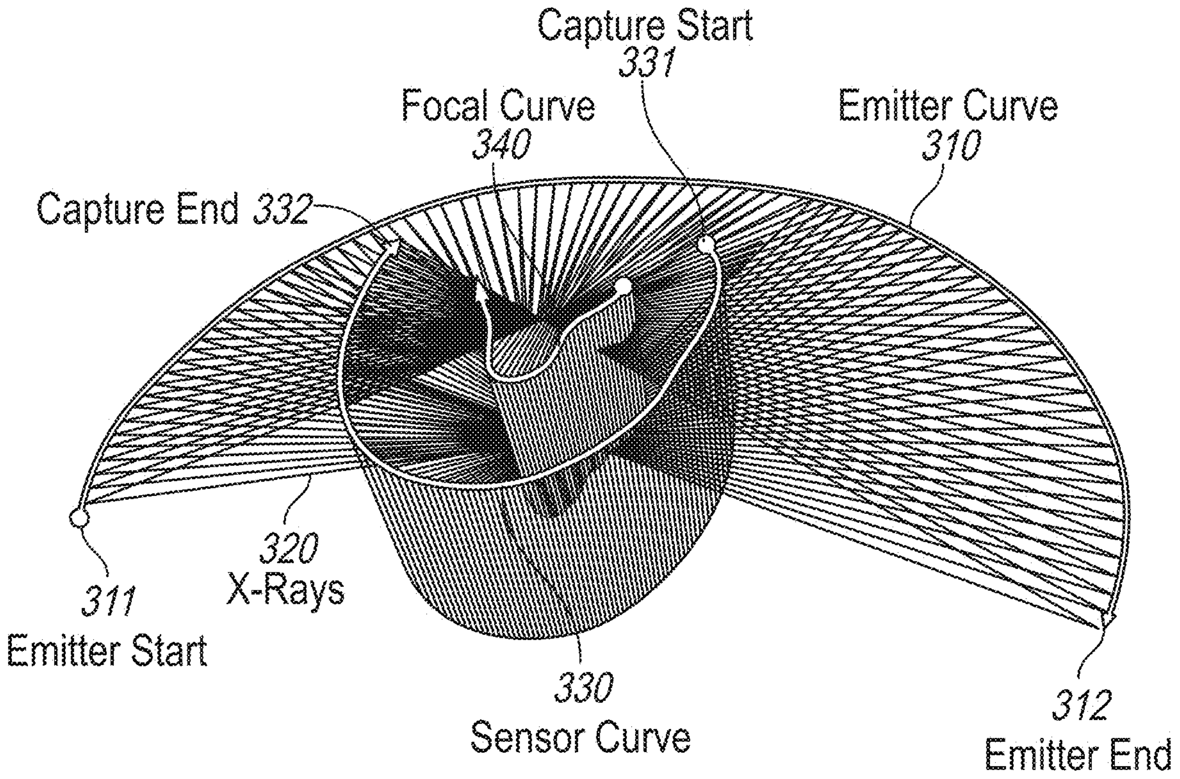
FIG. 3 depicts a panoramic arrangement of x-ray emission and sensing using an extra-oral x-ray system, according to an example.

The x-ray system 100 is adapted for performing dental panoramic imaging procedures, including for generating panoramic and CEPH images using the techniques discussed below. As shown in FIG. 1, the x-ray system 100 comprises an x-ray emitter array 103 having at least two individual x-ray emitters, each capable of emitting x-ray radiation (e.g., as depicted in FIG. 3), which are offset at least along a predetermined direction (e.g., in the height direction or longitudinal direction of the patient). The x-ray device 101 further comprises an x-ray detector 104 for at least partially detecting the x-ray radiations emitted by the individual x-ray emitters during one revolution. For instance, the x-ray emitter array 103 and the x-ray detector 104 may be arranged movably relative to one another about an axis running parallel to the predetermined direction, where the areas of the x-ray detector 104 respectively irradiated by the individual x-ray emitters at least partially overlap.

The x-ray device 101 may further include an aperture mechanism (not shown) for collimating the x-ray radiation emitted by the individual x-ray emitters onto the respective areas to be irradiated. The x-ray device 101 may further include a control device or mechanism (not shown) for moving the x-ray emitter array 103 and the x-ray detector 104 around the parallel axis, and for controlling the individual x-ray emitters and for reading out the image series of the respective irradiated surfaces of the x-ray detector 104 during the rotation. These and other features may be controlled by on-board logic and processing circuitry on the x-ray device 101, which may be controlled by the operator device 105 in some examples.

The computing system 110 is depicted as including processing circuitry 112, memory 114, and a storage device 116. The processing circuitry 112 may execute machine-readable software instructions (e.g., provided from the memory 114 or the storage device) to perform operations that implement panoramic image data processing 122, cephalometric image data processing 124, and a graphical user interface 126, as discussed below. The image processing methods discussed herein may be computer-implemented methods and can be executed via coordination of the x-ray device 101, the computing system 110, or the x-ray system 100 which includes both sub-systems. Further example implementations of the processing circuitry 112, the memory 114, and the storage device 116, are provided below with reference to FIG. 10.

The image processing methods performed by the computing system 110 may include the panoramic image data processing 122 and the cephalometric image data processing 124. Further details on the creation of a panoramic image via the panoramic image data processing 122 and the creation of a cephalometric image via the cephalometric image data processing 124 are discussed in FIGS. 2 to 9, below. The panoramic image and the cephalometric image may be separately or jointly presented via a graphical user interface 126, such as an image display user interface that is controlled via an input device 144 and presented via the output device 142. Other image data processing of the computing system 110 may be invoked via the graphical user interface 126 or the operator device 105.

Figure 7:
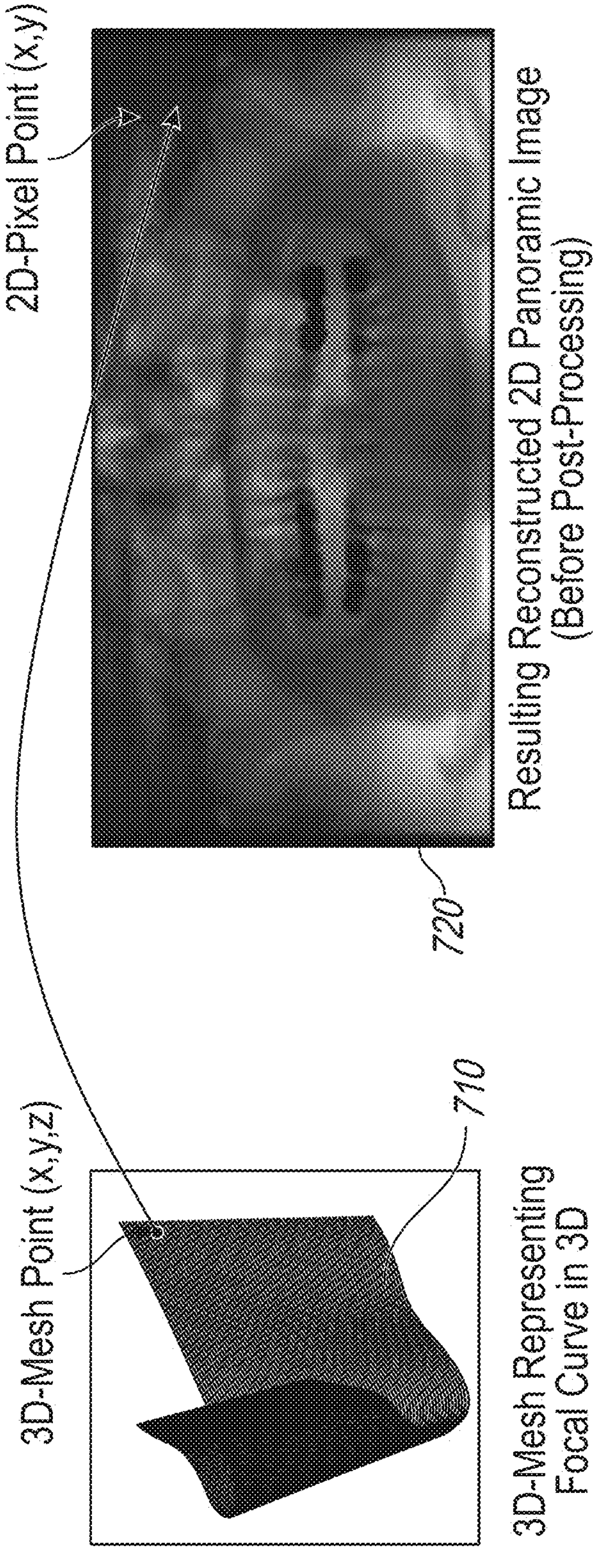
FIG. 7 depicts a mapping between a three-dimensional space and a reconstructed panoramic image, according to an example.

The panoramic image data processing 122 may include the creation of a spatial panoramic image based on projection images in captured FFPAN image data. For instance, respective FFPAN images produced from x-rays (e.g., x-rays 320 shown in FIG. 3) can be reconstructed into a 2D spatial panoramic image (e.g., panoramic image 720 shown in FIG. 7). The creation of this panoramic image may be assisted with a defined shape such as a 3D mesh that represents a focal curve in a 3D space (e.g., focal curve 340 shown in FIG. 3) and is used for establishing a focal layer of a specific thickness (e.g., a focal layer with a default focal layer thickness 440 or an extended focal layer thickness 445 shown in FIG. 4). In some examples, this default focal layer in 3D space can be further optimized locally by an autofocus algorithm during the reconstruction of the panoramic image. An illustration of the relationship between the 3D mesh and a resulting 2D panoramic image is shown in FIG. 7.

Figure 8:
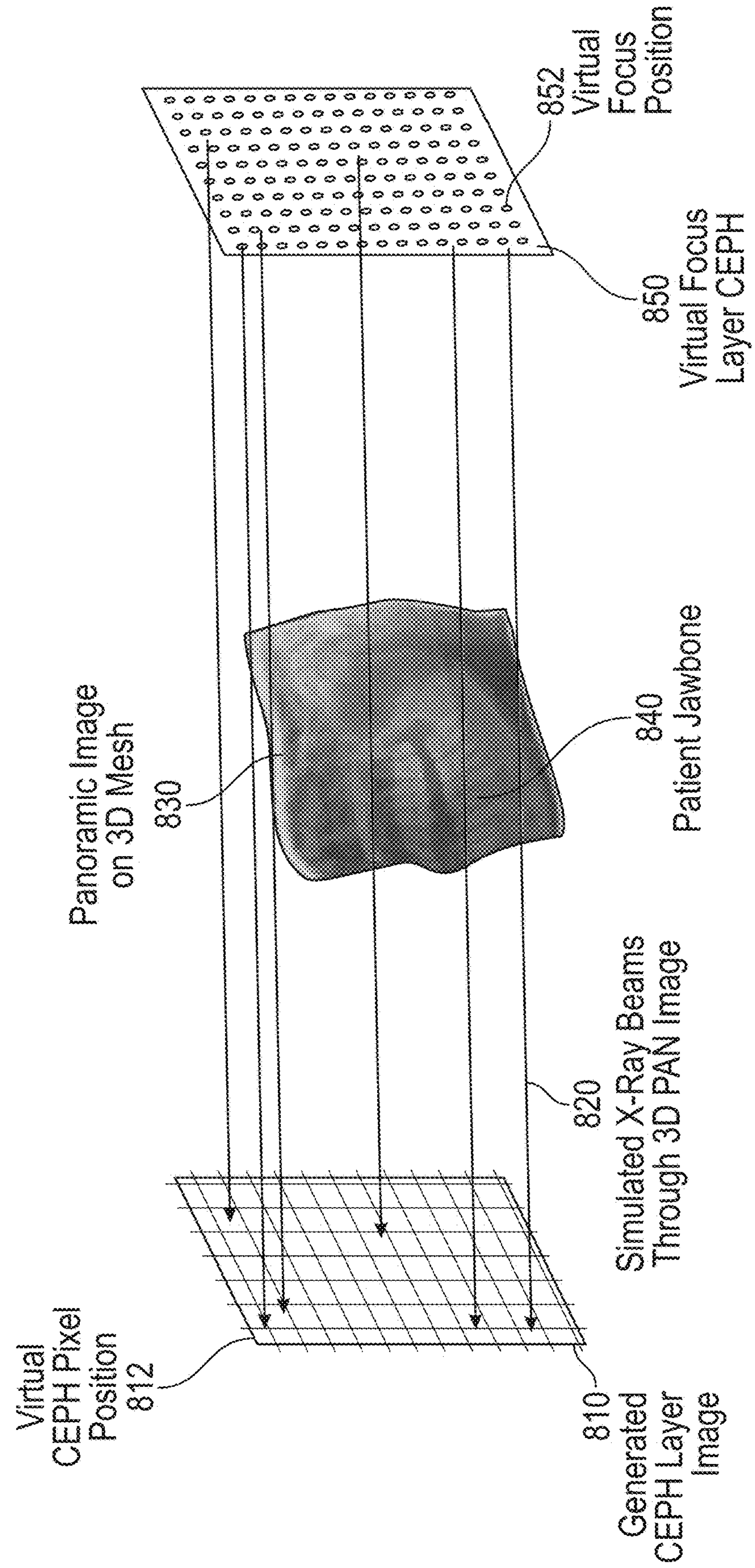
FIG. 8 depicts the creation of a virtual CEPH projection image based on simulated x-rays in a defined three-dimensional space, according to an example.

In a first approach, the cephalometric image data processing 124 may include calculating one or more virtual CEPH projection images using data from the 2D spatial panoramic image, and then reconstructing a virtual CEPH image from these virtual CEPH projection images. For instance, after the spatial panoramic image is represented in a defined 3D space, a number of virtual CEPH projection images can be re-created using simulated rays in the defined 3D space. In a second alternative approach, the cephalometric image data processing 124 may include calculating a virtual CEPH projection image after defining a dimension and a resolution of the CEPH image in a defined 3D space, and using simulated x-ray beams in the defined 3D space (e.g., one beam per pixel) to create a computed CEPH image. An illustration of the example geometry and simulated x-rays used for creating a computed CEPH image is shown in FIG. 8.

Methods for calculating CEPH views based on FFPAN image data from extraoral X-ray systems are not provided in the current state of the art. Rather, in the current state of the art, CEPH images may be produced using separate CEPH imaging devices added to extraoral X-ray systems (e.g., with a CEPH arm as discussed above), or based on special processing of 3D image data (e.g., volumetric images) produced from 3D imaging systems (e.g., CBCT scanners). It will be appreciated that the present approaches for calculating CEPH views based on a reconstructed 2D panoramic image are distinguishable from prior approaches for producing CEPH views based on a 3D image volume. The use of CBCT and other 3D scanning procedures is associated with an increased radiation dose for the patient and a reduced resolution of a resulting CEPH view, whereas there may be many scenarios where only a 2D panoramic image is captured and only source FFPAN image data is available.

The present approaches for calculating CEPH views based on panoramic images and FFPAN image data—which is already captured during standard evaluation procedures in many dental and orthodontic practices—provide a number of technical and operational benefits. These benefits include but are not limited to: reduced equipment requirements because a dedicated CEPH arm is not required; reduced radiation dose for the patient, because separate exposure from the CEPH arm or 3D scanning is not needed; and creation of an image with a resolution of the calculated CEPH view similar to a conventional CEPH image. The techniques discussed herein can be used to avoid the capture of separate x-ray images, allowing a radiation dose reduction closer to ALARA (as low as reasonably achievable) goals. These and other benefits can be achieved while using the same patient positioning of panorama shots used with existing panoramic x-ray capture workflows.

Figure 2:
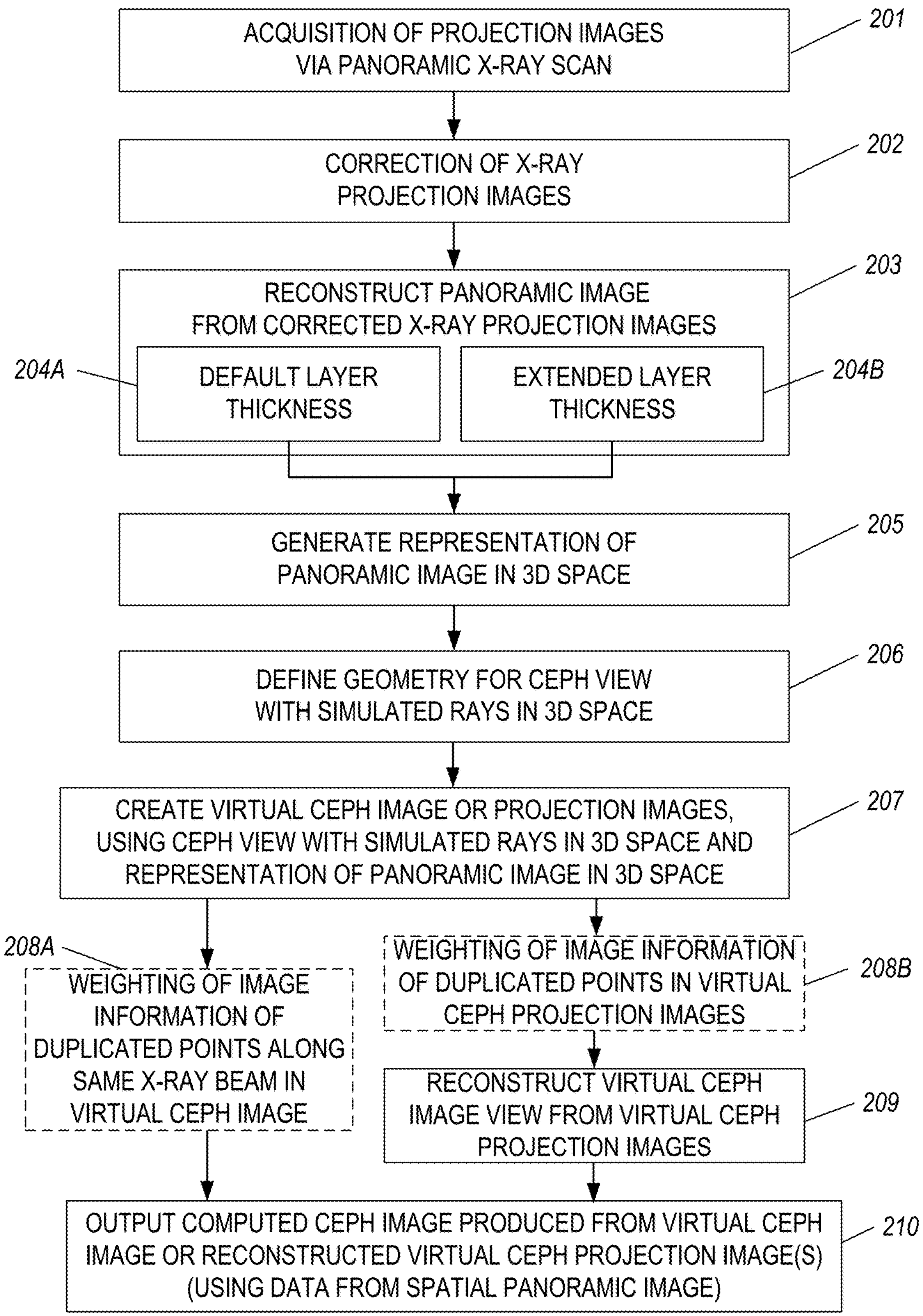
FIG. 2 depicts a flowchart of an algorithm for calculating CEPH views based on panoramic imaging data, according to an example.

FIG. 2 depicts a flowchart of an example algorithm for calculating CEPH views based on panoramic imaging data. Although this flowchart depicts a sequence of operations, some of the operations may be repeated or performed in an alternate sequence.

Operation 201 depicts an acquisition of raw imaging data (e.g., individual x-ray projection images) via a panoramic x-ray scan. For example, this may include the use of the x-ray system 100 to obtain many FFPAN images at a pre-defined frame capture rate (e.g., 300 frames per second). FIG. 3, discussed below, depicts an example panoramic x-ray scan procedure used to capture respective projection images, such as may be performed by rotation of the x-ray device 101 around a human subject.

Operation 202 depicts correction of the raw image data (e.g., the x-ray projection images) acquired from the panoramic x-ray scan. This may include image correction techniques such as dark-field correction, gain or flat-field correction, defect correction, or other corrections (e.g., scatter removal, noise reduction, contrast enhancement, etc.). Other image correction techniques may be utilized.

Figure 4:
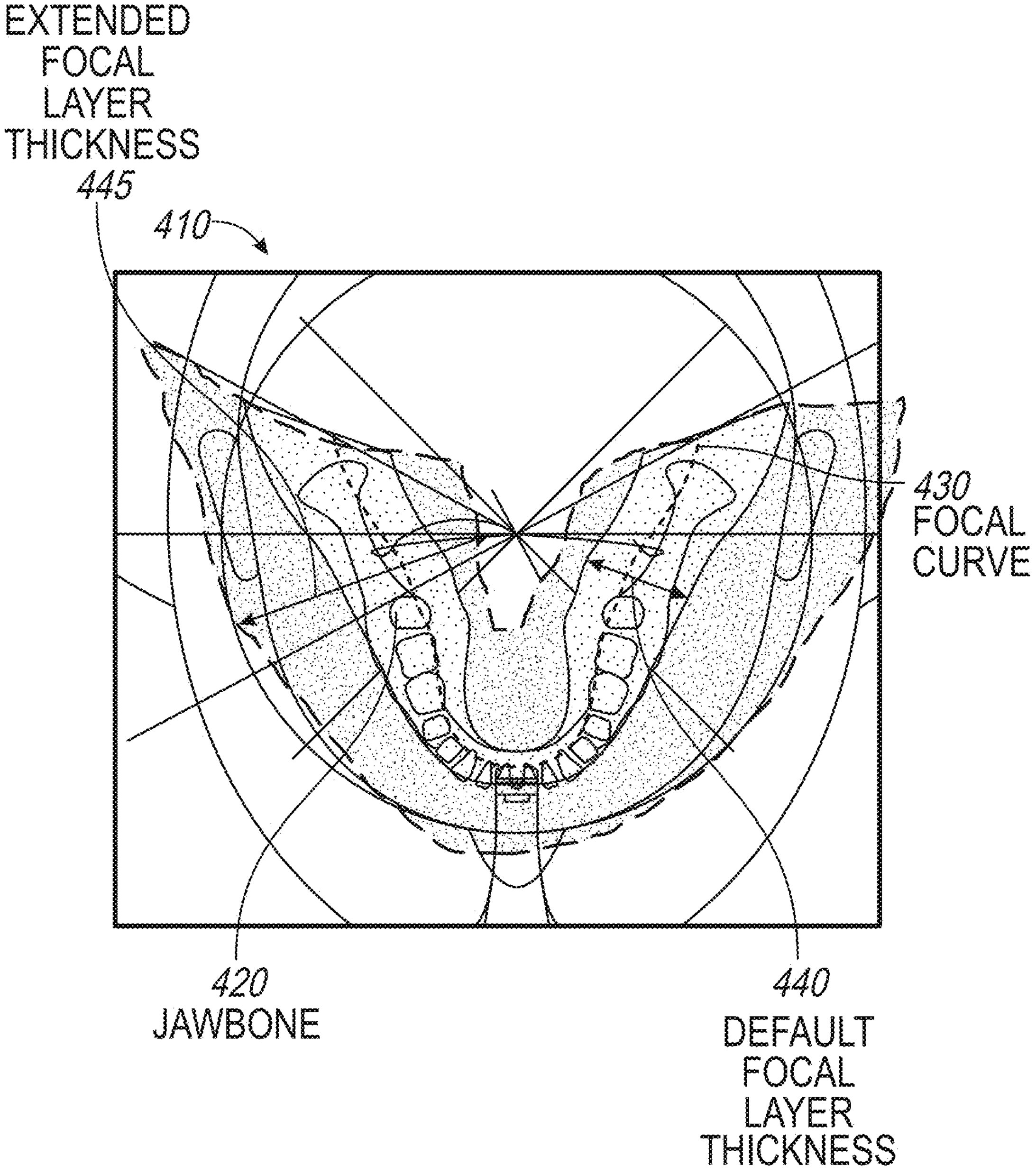
FIG. 4 depicts a panoramic focal curve and focal layers in a cross-sectional view of patient anatomy, according to an example.

Operation 203 depicts reconstruction of a panoramic image from the corrected x-ray projection images. As an example, the reconstruction of the panoramic image may use a focal layer with a default focal layer thickness with operation 204A. In another example, the reconstruction of the panoramic image may use a focal layer with an extended or expanded focal layer thickness with operation 204B. A comparison of a focal layer with a default thickness and a focal layer with an extended thickness is shown in FIG. 4 and discussed below.

Operation 205 includes generating a representation of the panoramic image in a defined 3D space. As an example, this may include generating a 3D shape such as a curved mesh (a "3D Mesh") that represents the focal curve in a three-dimensional space. An illustration of how this 3D shape corresponds to a panoramic image is shown in FIG. 7. Other detailed examples of how a panoramic image may be reconstructed and represented in a defined 3D space are provided in European Patent Application Publication No. EP4375928A1 by inventor Stefan Eichner, titled "METHOD FOR LENGTH MEASUREMENT WITHIN DENTAL PANORAMIC IMAGES", which is incorporated by reference herein in its entirety.

Operation 206 includes defining a geometry for a CEPH view with simulated rays in the defined 3D space. As an example, this may include determining at least one new focus position and virtual focus layer for a CEPH view in the defined 3D space, to define how simulated x-ray beams would travel through the representation of the panoramic image that exists in the defined 3D space. This is shown with reference to FIG. 8, with the depiction of a virtual focus position 852, a virtual focus layer 850, and simulated x-ray beams 820.

Operation 207 includes creating a virtual CEPH image or multiple virtual CEPH projection images, using a CEPH view established from simulated x-rays that travel through the mesh representation of the panoramic image in the defined 3D space. In a first example, the virtual CEPH image is created by intersecting the simulated x-rays in the defined three-dimensional space through the voxels of the three-dimensional mesh to a virtual cephalometric image, and modeling one x-ray beam per pixel of the virtual cephalometric image. In a second alternative example, the virtual CEPH projection images are produced by intersecting the simulated x-rays in the defined three-dimensional space through the voxels of the three-dimensional mesh, and creating the virtual cephalometric projection images from the intersected voxels of the three-dimensional mesh.

An example modeling of this defined 3D space is shown in FIG. 8, with the depiction of pixel positions (e.g., pixel position 812) of a generated CEPH layer 810 that corresponds to data of the simulated x-ray beams. Thus, as the simulated x-ray beams 820 travel through the 3D panoramic image 830, individual pixels from the panoramic image may be selected for use in a virtual CEPH image or in a virtual CEPH projection image.

If a virtual CEPH image is created, then Operation 208A may be used; if virtual CEPH projection images are created, then Operation 208B may be used. Operation 208A is an optional procedure of weighting image information for duplicated points along a same x-ray beam in the virtual CEPH image. Operation 208B is an optional procedure of weighting image information for duplicate points in the new virtual CEPH projection images. This additional weighting of the imaging information may be applied depending on the position of the virtual CEPH image view to be calculated. Operation 209 also depicts reconstructing a virtual CEPH image view from the various virtual CEPH projection images to produce a computed CEPH image. Additional image post-processing techniques (e.g., image correction techniques, changes to image brightness or contrast, etc.) may be performed on the individual virtual CEPH projection images or performed on the computed CEPH image. As will be understood, the same (or different) post-processing or image correction techniques may be used on the reconstructed panoramic image and the created CEPH image.

Operation 210 depicts outputting the computed CEPH image that was produced from the virtual CEPH image or reconstructed from the virtual CEPH projection images. This may include saving the computed CEPH image in a 2D image format in computer memory or storage, providing the computed CEPH image data to another computing device via a network, or outputting the computed CEPH image to a display screen.

Although the preceding operations refer to the capture of new images from a panoramic x-ray scan (e.g., with operation 201), it will be understood that the remaining operations can be used to create a panoramic image and a computed CEPH image from previously captured FFPAN image data. Based on the acquisition geometry of the panoramic scan acquisition data from the extra-oral X-ray system used and the typical geometry ratios of a classic CEPH image, a virtual focus position, simulated x-rays, and mapped image data may be used to create virtual CEPH projection images and reconstruct a computed CEPH image.

FIG. 3 depicts an example panoramic arrangement of x-ray emission positions relative to sensing positions in an extra-oral x-ray system. Specifically, FIG. 3 depicts how a series of hundreds or thousands of x-rays 320 are emitted along an emitter curve 310, starting at an emitter start position 311 and ending at an emitter end position 312. The x-rays 320 are received using at least one sensor that travels along a sensor curve 330, starting at a capture start position 331 and ending at a capture end position 332. Although the x-ray sensor travels in a circular-like or "U" like shape along the sensor curve 330, the focal area of the panoramic image will optimally vary depending on the particular geometric shape of the patient's dentition. Thus, the x-ray device may establish a focal curve 340 which has a shape that is different from the shape of the x-ray emitter curve 310 and the sensor curve 330.

The shape of the focal curve 340 may be constructed in a three-dimensional space and used for subsequent image processing. For instance, a construction of the panoramic image (and the resulting computed CEPH image produced from the panoramic image) may be based on the use of a 3D mesh that represents the focal curve 340 in three coordinates (x, y, z) in a three-dimensional space.

FIG. 4 depicts a cross-sectional view of patient anatomy 410, showing how a shape of a focal curve 430 of a panoramic scan corresponds to a jawbone 420 of an example patient anatomy of the patient's jawbone and dentition. The focal curve 430 that is depicted follows the general outline of the bone and interior side of teeth and is used to shape a focal layer that defines the objects to be displayed.

FIG. 4 also depicts an area captured in the patient anatomy when portrayed with a default focal layer thickness 440 versus an extended focal layer thickness 445. The focal layer thickness is a range around the focal layer (extending in lingual and buccal directions) that defines the amount of blurring of the objects outside the focal layer. The larger the focal layer thickness, the lower the sharpness of the objects along the focal layer. The default focal layer thickness 440 may be used in a panoramic image to provide a focus on the area immediately in and around the jawbone and connected teeth. The extended focal layer thickness 445 may be used to provide an expanded view of patient anatomy for a computed CEPH image, to depict additional characteristics of the patient's face.

In particular, a typical perspective and character of a classic CEPH image can be realized by extending the focal layer thickness. As two non-limiting examples, an extension of the focal layer thickness can be created by omitting or skipping raw image frames (e.g., omitting x-ray projection images, as depicted in FIG. 5) or with use of a weighted collimator beam profile (e.g., by applying weighting to a collimator beam profile of the projection images, as depicted in FIG. 6).

Figure 5:
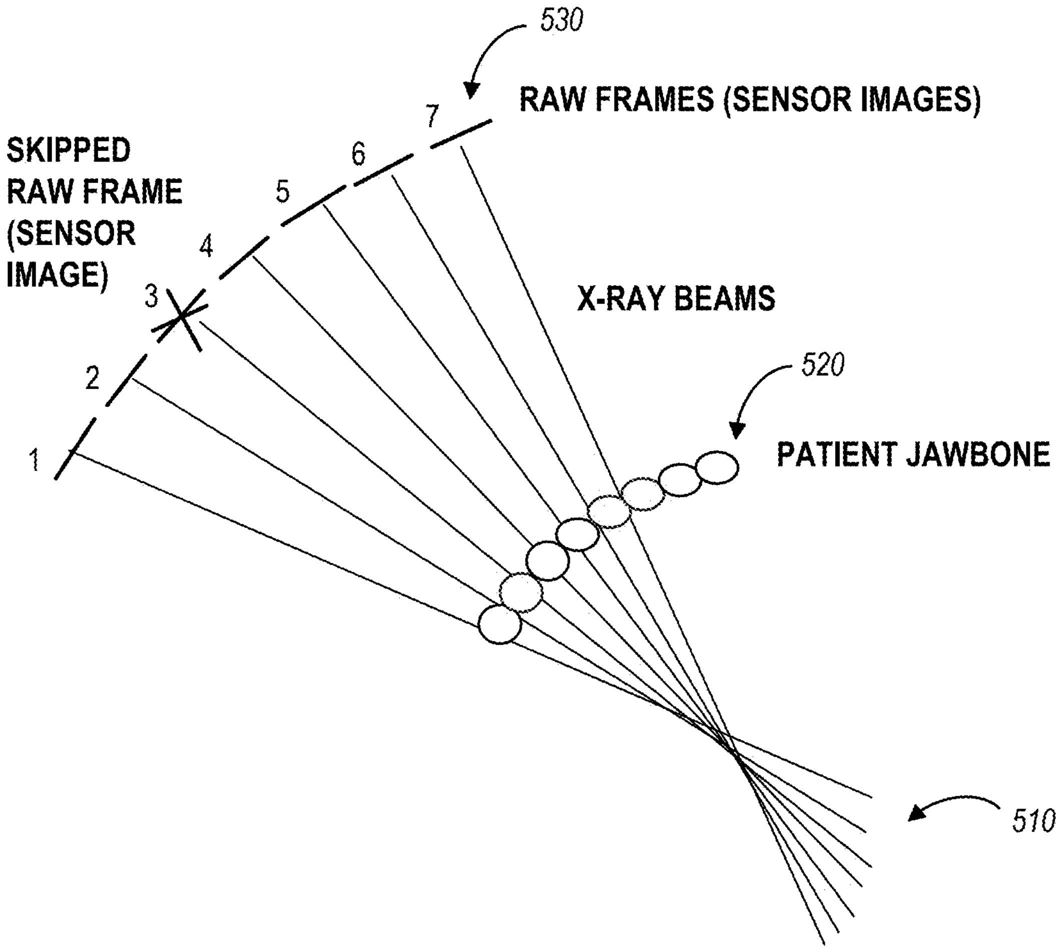
FIGS. 5 and 6 depict techniques for refining projection images used to reconstruct a panoramic image, according to an example.

FIG. 5 depicts a first approach for refining projection images used to reconstruct a panoramic image, based on excluding information from certain views. As shown, a series of x-rays 510 are emitted through patient anatomy to produce a series of raw image frames 530 (e.g., projection images). This is shown as the x-rays progressively cross and intersect a patient's jawbone 520. However, some of the raw image frames 530 can be skipped and excluded for use when reconstructing the panoramic image. For example, particular frames may be skipped because the images correspond to beam angles that are not usable in a CEPH view, or to further increase the focal layer thickness.

Figure 6:
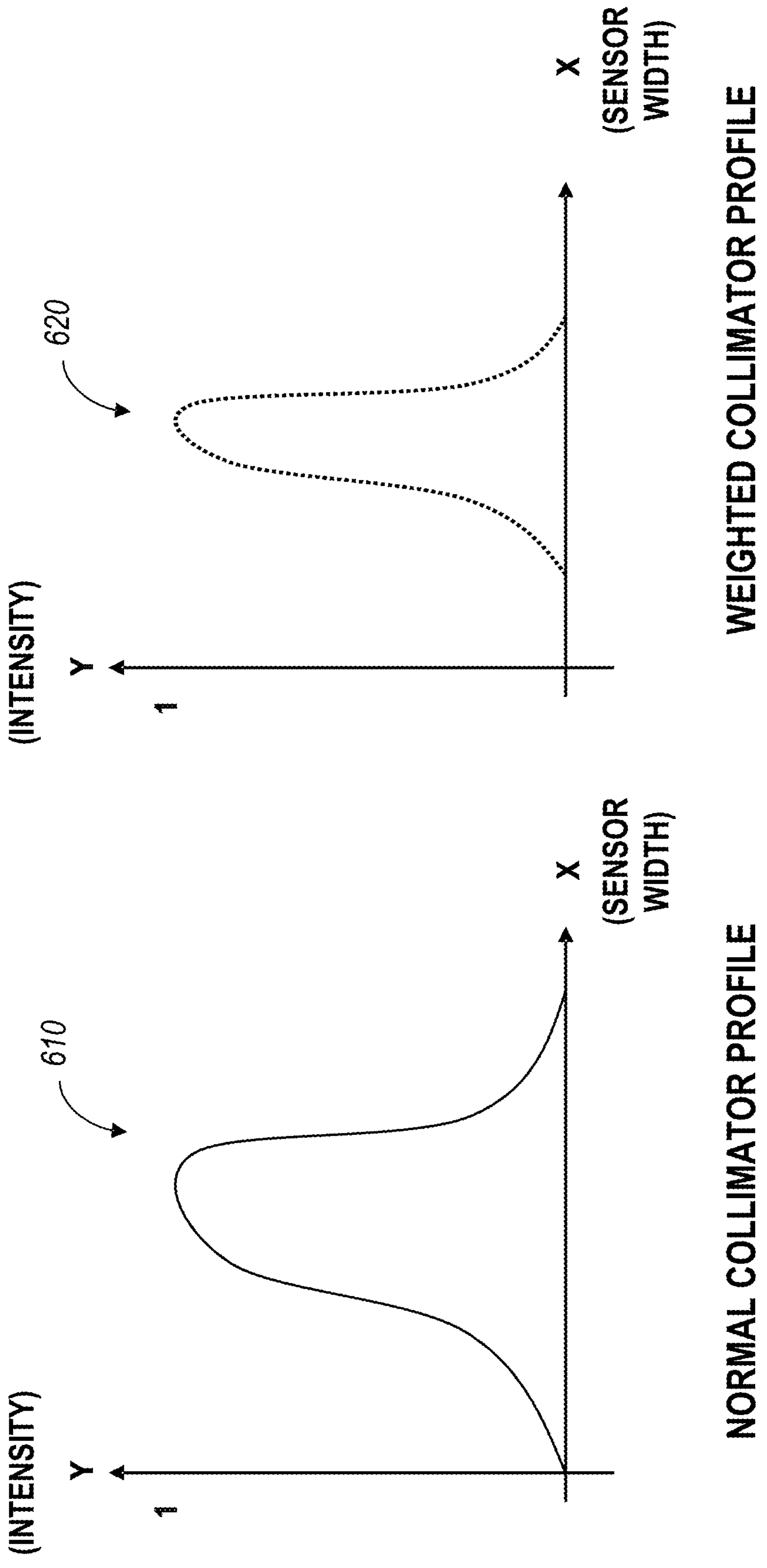

FIG. 6 depicts a second approach for refining projection images used to reconstruct a panoramic image, based on weighing information represented in the projection images. For example, a normal collimator beam profile 610 may be changed into a weighted collimator beam profile 620 within a raw projection image or image frame used for constructing a panoramic scan. The beam profile, e.g., depicted in FIG. 6, is similar to a Gaussian shape and defines the amount of radiation acquired during the scan. If the beam profile is reduced in size (e.g., shrunk) on both sides, then less information is provided for the reconstruction results.

By reducing the beam profile, the covered beam angle per projection frame is then decreased. This will cause an increased focal layer thickness as fewer pixels are combined with each other in the reconstructed image. The narrower the beam profile, the larger the resulting thickness of the focal layer. Thus, either approach of FIG. 5 or FIG. 6 may be used to increase the slice thickness of the spatial panoramic image resulting from reconstruction—and thus increase the amount of information that is provided in a computed CEPH image created from the reconstructed panoramic image.

FIG. 7 depicts a mapping between a three-dimensional space and a reconstructed panoramic image. This illustration shows how a 3D mesh 710 represents or corresponds to the shape of a focal curve in a 3D space (e.g., focal curve 340, focal curve 430). The 3D mesh 710 also defines a series of points (voxels) in the 3D space that map to individual points (pixels) of a 2D panoramic image 720. The reconstructed 2D panoramic image 720 represents the information that would be presented if the 3D mesh 710 was illustrated as a 2D layer. Thus, when the representation of the reconstructed 2D panoramic image 720 is placed in the 3D space (e.g., at operation 205), the shape of the resulting 3D object will resemble the 3D mesh 710.

FIG. 8 depicts the creation of a virtual CEPH projection image based on simulated x-rays in a defined three-dimensional space. Specifically, a 3D panoramic image 830 that depicts the patient's jawbone 840 is represented in this 3D space. The 3D panoramic image 830 is oriented and shaped based on the 3D mesh (e.g., 3D mesh 710) that was used for the panoramic image reconstruction. Specifically, this 3D mesh represents a focal curve of the two-dimensional panoramic image in the geometry of the panoramic scan. The right side of this illustration shows a virtual focus layer 850 for the CEPH projection image. The left side of this depiction shows a resulting virtual CEPH projection image at CEPH layer 810, and the distance between these two layers is based on CEPH view geometry.

FIG. 8 also depicts how multiple virtual x-ray beams from a simulated x-ray source in this 3D space intersect the 3D panoramic image 830 that has been shaped based on the 3D mesh. Information from the virtual x-ray beams is accumulated, weighed, and stored in the related pixel position (e.g., pixel position 812) of the generated CEPH layer 810. The distances in the 3D space among the generated CEPH layer

810, the virtual focus layer 850, and the 3D panoramic image 830 are selected based on the geometrical relationships used for capturing a conventional CEPH scan.

The present approaches for calculating CEPH views based on panoramic images can also be optionally extended to calculate CEPH views from different spatial directions (e.g., other than a conventional lateral direction). The present approaches for calculating CEPH views also can be applicable to FFPAN image data retrospectively, based on analysis of existing projection image data and without requiring new raw data to be captured for a CEPH view.

Because FFPAN projection images are limited in height, the resulting computed CEPH images may have a reduced height as compared with a classic CEPH view. If necessary, this limitation can be addressed with one of the following techniques that creates a two-dimensional panoramic image with an expanded image height. A first technique may include combining two height-shifted projection images (e.g., captured from a dedicated FFPAN sensor), using a technique that combines the image data in a geometrically correct manner (e.g., with/without markers for registration of the FFPAN image data). A second technique may include a change to the readout range used with an x-ray sensor, such as by extending the height of the vertical dimension of a sensor's active area to capture additional information used for the CEPH view. Other techniques such as the use of trained artificial intelligence models and algorithms may also be applied.

Figure 9:
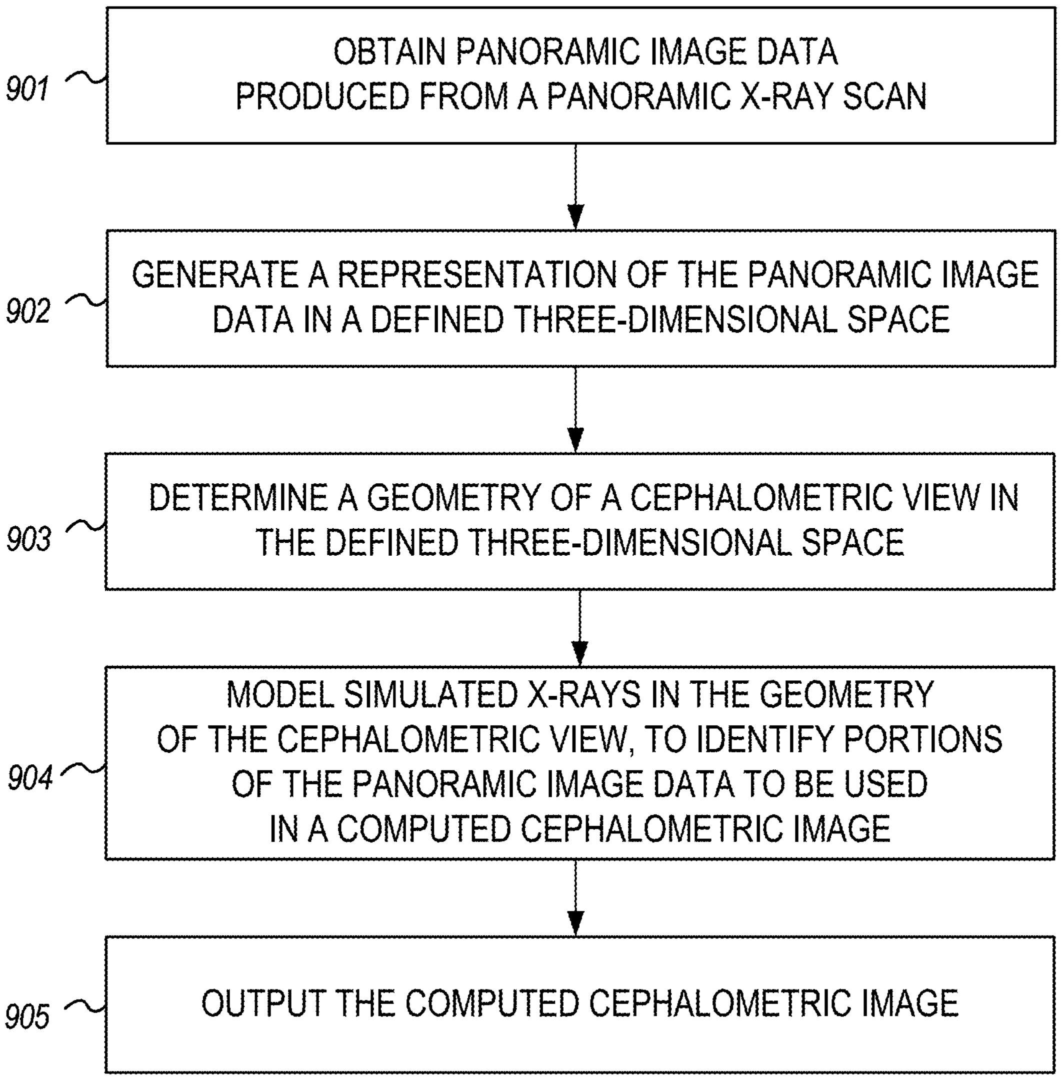
FIG. 9 illustrates a flowchart of a method for generating a computed cephalometric image, according to an example.

FIG. 9 depicts a flowchart of an example method of generating a computed cephalometric image. This method may be implemented by a machine-readable medium (e.g., computer-readable medium) including instructions, which when executed by processing circuitry, cause the processing circuitry to perform the following operations. In another example, this method may be implemented by an x-ray system, comprising: an x-ray source and an x-ray detector for acquiring panoramic image data, and a computing unit for performing the following operations. In another example, this method may be implemented by a computer system comprising memory storing panoramic image data and at least one processor configured to perform the following operations.

Operation 901 includes obtaining panoramic image data produced from a panoramic x-ray scan. This may correspond to aspects of operation 201 discussed above, including with the use of the x-ray system 100 discussed above. In a specific example, the panoramic image data comprises a two-dimensional panoramic image, and the method also includes reconstructing the two-dimensional panoramic image from a plurality of x-ray projection images, as in operation 203 discussed above. For instance, the plurality of x-ray projection images may be captured in the extraoral x-ray system 100 with a full-frame panoramic (FFPAN) scan. The method may also include performing at least one image correction technique on the plurality of x-ray projection images, as in operation 202 discussed above, or performing at least one image correction technique on the reconstruction of the two-dimensional panoramic image.

In further examples, the reconstruction of the two-dimensional panoramic image from the plurality of x-ray projection images, as in operation 203 discussed above, includes extending a focal layer thickness of a focal layer (e.g., as discussed with reference to FIG. 4). Establishing this extended focal layer thickness may include at least one of: omitting respective frames of the plurality of x-ray projection images for use in reconstructing the two-dimensional panoramic image (e.g., as discussed with reference to FIG. 5) or using a weighted collimator beam profile of at least one projection image of the plurality of x-ray projection images used in reconstructing the two-dimensional panoramic image (e.g., as discussed with reference to FIG. 6). In still further examples, reconstructing the two-dimensional panoramic image includes combining two (or more) height-shifted projection images to create the two-dimensional panoramic image with an expanded image height.

Operation 902 includes generating a representation of the panoramic image data in a defined three-dimensional space. This operation may correspond to aspects of operation 205 discussed above and may include mapping pixel data of a two-dimensional panoramic image to voxels of a three-dimensional mesh in the defined three-dimensional space, such as is discussed with reference to FIG. 7. This three-dimensional mesh may correspond to a focal curve of the two-dimensional panoramic image in a geometry of the panoramic x-ray scan.

Operation 903 includes determining a geometry of a cephalometric view in the defined three-dimensional space. This operation may correspond to aspects of operation 206, as discussed above, and may include determining a dimension and resolution of the CEPH image in the 3D space, relative to the representation of the panoramic image data and the generated CEPH layer, as discussed with reference to FIG. 8. Variations to the geometry of a cephalometric view may be based on changes to the known temporal acquisition geometry of the source panoramic imaging data and the acquisition geometry of the desired cephalometric view.

Operation 904 includes modeling simulated x-rays in the geometry of the cephalometric view to identify portions of the panoramic image data to be used in a computed cephalometric image. This operation may correspond to aspects of operations 206 and 207 as discussed above. Modeling the simulated x-rays may include use of alternative approaches. A first approach for modeling involves creation of virtual cephalometric projection images, followed by reconstructing these projection images into a cephalometric image. A second approach for modeling involves modeling one x-ray beam, per pixel, of the cephalometric image. In the second approach, there is no need for the creation of virtual cephalometric projection images and reconstruction.

In connection with the first approach, modeling the simulated x-rays may include intersecting the simulated x-rays in the defined three-dimensional space through the voxels of the three-dimensional mesh, as the method also includes creating a plurality of virtual cephalometric projection images from the voxels of the three-dimensional mesh and reconstructing of the computed cephalometric image from the plurality of virtual cephalometric projection images. Additionally, weighing may be performed on image information of duplicated points in the plurality of virtual cephalometric projection images, such as may correspond to aspects of operation 208 discussed above. In connection with the second approach, modeling the simulated x-rays may include intersecting the simulated x-rays in the defined three-dimensional space through the voxels of the three-dimensional mesh to a virtual cephalometric image, as the method also includes modeling one x-ray beam per pixel of the virtual cephalometric image and creating the computed cephalometric image from pixels of the virtual cephalometric image. Additionally, weighing may be performed on image information of duplicated points along a same x-ray beam corresponding to a pixel in the virtual cephalometric image.

As discussed with reference to FIG. 8, the simulated x-rays may correspond to at least one virtual focus position originating from a virtual focus layer, where the virtual focus layer corresponds to a simulated x-ray source in the geometry of the cephalometric view. In further examples, the simulated x-rays extend in the defined three-dimensional space from the virtual focus layer, through a three-dimensional modeling of the panoramic image data, to a virtual projection image or a virtual cephalometric image constructed at a generated layer. Additionally, respective distances in the defined three-dimensional space among the virtual focus layer, the three-dimensional modeling of the panoramic image data, and the generated layer may be established based on geometrical relationships used for cephalometric imaging.

Operation 905 includes outputting the computed cephalometric image. This operation may correspond to aspects of operation 210, discussed above. In some examples, image post-processing and correction/adjustment techniques may be performed on the computed cephalometric image before or after outputting.

The techniques discussed herein may produce computed CEPH images to assist dental treatments, such as restorative treatments, endodontic treatments, periodontal treatments, implant treatments, aligner treatments, orthodontic treatments, and the like. Such computed CEPH images therefore may be used to provide therapeutic and diagnostic information related to teeth, roots, nerve canals, temporomandibular joints, jaw bones, and the like. Moreover, the example embodiments described herein are not limited to FFPAN panoramic imaging capture techniques but may also apply to panoramic images produced by other modalities and techniques.

As will be appreciated, the example aspects described herein can be implemented using a single computer or using a computer system that includes multiple computers, each programmed with control logic to perform various of the above-described functions. Embodiments may be implemented in hardware (e.g., circuitry), firmware, software, or any combination thereof. Embodiments may also be implemented as instructions stored on a machine-readable medium, which may be read and executed by one or more processors (e.g., implementations of processor circuitry).

Figure 10:
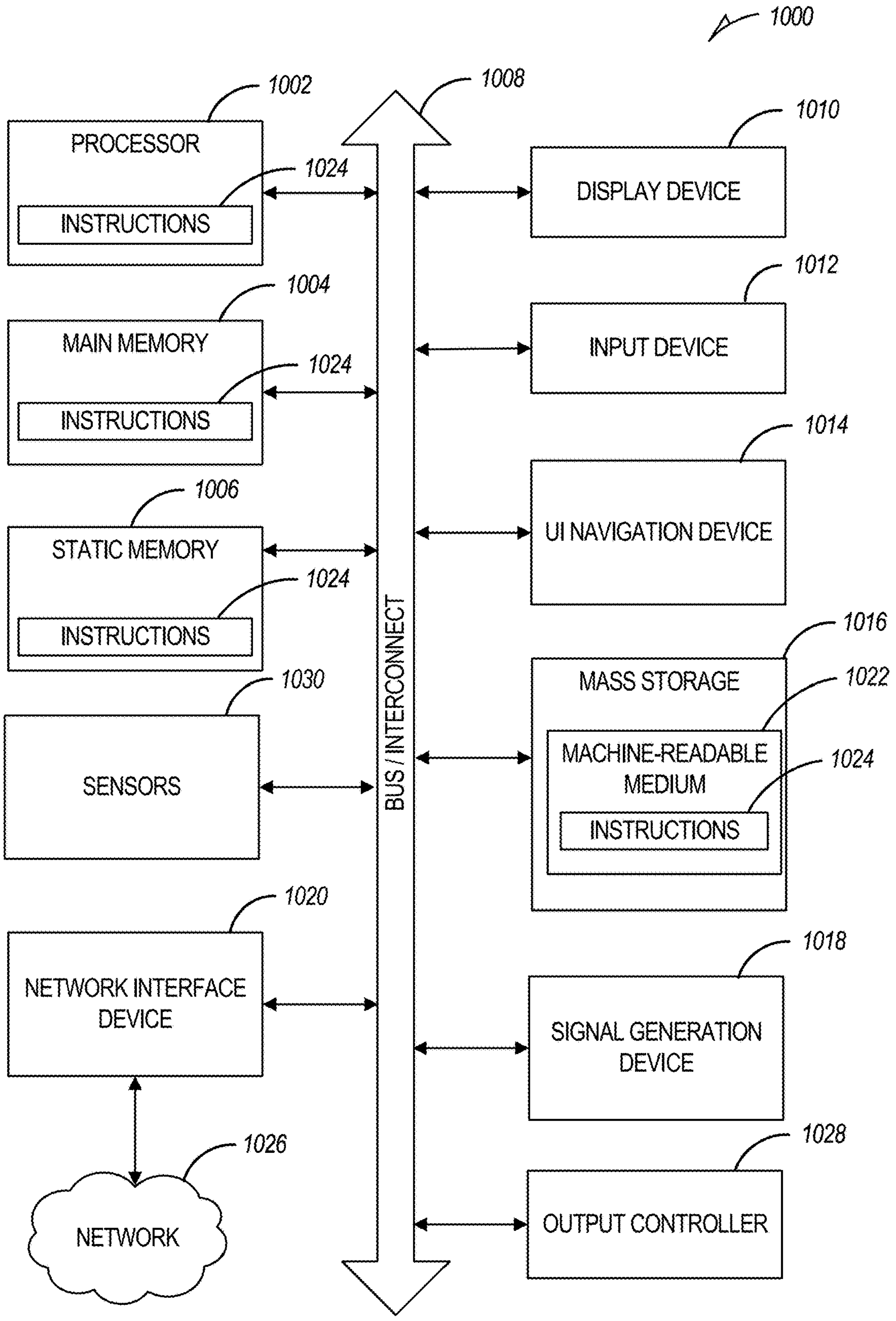
FIG. 10 depicts a block diagram of an example of a computing system upon which any one or more of the techniques discussed herein may be performed, according to an example.

FIG. 10 depicts a block diagram of an example of a computing system 1000 (or a suitable apparatus, device, system or machine) upon which any one or more of the techniques (e.g., methods) discussed herein may be performed. In alternative embodiments, the system 1000 may operate as a standalone device or may be connected (e.g., networked) to other machines. In a networked deployment, the system 1000 may operate in the capacity of a server machine, a client machine, or both in server-client network environments. The system 1000 may be a personal computer (PC), a tablet PC, server computer, a mobile telephone, a web appliance, a networked device, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The system 1000 may receive a user command by way of any of input device 1012, UI navigation device 1014, display device 1010, or signals from remote systems (e.g., received via network 1026). The system 1000 may output an indication that an action has been performed by way of any of display device 1010 and signal generation device 1018. The system 1000 also may provide output of the computed cephalometric image in a machine readable medium 1022 based on the techniques to generate the computed cephalometric image as described herein. The system 1000 may be used to implement the operations performed by the method of generating a computed cephalometric image (e.g., as discussed with reference to FIG. 9), and related data processing operations involved in processing, reconstructing, modeling, representing, and visualizing related data.

System 1000 (e.g., computer system) may include processing circuitry such as a hardware processor 1002 (e.g., a central processing unit (CPU), a graphics processing unit (GPU), a hardware processor core, field programmable gate array (FPGA), or any combination thereof), a main memory 1004 and a static memory 1006, some or all of which may communicate with each other via an interlink (e.g., bus) 1008. The system 1000 may further include a display device 1010, an input device 1012 (e.g., a keyboard or other alphanumeric input device), and a user interface UI navigation device 1014 (e.g., a mouse). In an example, the display device 1010, input device 1012 and UI navigation device 1014 may be integrated into a touch screen display. The system 1000 may additionally include a mass storage device 1016 (e.g., drive unit or other similar storage device or unit), a signal generation device 1018 (e.g., a speaker), a network interface device 1020 connected to a network 1026, and one or more sensors 1030. The system 1000 may include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The mass storage device 1016 may include a machine readable medium 1022 on which is stored one or more sets of data structures or instructions 1024 (e.g., software) embodying or used by any one or more of the techniques or functions described herein. The instructions 1024 may also reside, completely or at least partially, within the main memory 1004, within static memory 1006, or within the hardware processor 1002 during execution thereof by the system 1000. In an example, one or any combination of the hardware processor 1002, the main memory 1004, the static memory 1006, or the mass storage device 1016 may constitute machine readable media.

While the machine readable medium 1022 is illustrated as a single medium, the term "machine readable medium" may include a single medium or multiple media (e.g., a centralized or distributed database, and/or associated caches and servers) configured to store the one or more instructions 1024. The term "machine readable medium" may include any medium that is capable of storing, encoding, or carrying instructions for execution by the system 1000 and that cause the system 1000 to perform any one or more of the techniques of the present disclosure, or that is capable of storing, encoding, or carrying data structures used by or associated with such instructions. Non-limiting machine-readable medium examples may include solid-state memories, and optical and magnetic media. Specific examples of machine-readable media (e.g., one or more non-transitory storage medium) may include: read only memory (ROM); random access memory (RAM); non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Examples, as described herein, may include, or may operate by, logic or a number of components, or mechanisms, including in circuitry. Circuitry includes a collection of circuits implemented in tangible entities that include hardware (e.g., simple circuits, gates, logic, etc.). Circuitry membership may be flexible over time and underlying hardware variability. Circuitry includes members that may, alone or in combination, perform specified operations when operating. In an example, hardware of the circuitry may be immutably designed to carry out or conduct a specific operation (e.g., hardwired). In an example, the hardware of the circuitry may include variably connected physical components (e.g., execution units, transistors, simple circuits, etc.) including a computer readable medium physically modified (e.g., magnetically, electrically, moveable placement of invariant massed particles, etc.) to encode instructions of the specific operation. The instructions enable embedded hardware (e.g., the execution units or a loading mechanism) to create members of the circuitry in hardware via the variable connections to carry out or conduct portions of the specific operation when in operation. Accordingly, the computer readable medium is communicatively coupled to the other components of the circuitry when the device is operating. In an example, any of the physical components may be used in more than one member of more than one circuitry unit. For example, under operation, execution units may be used in a first circuit of a first circuitry unit at one point in time and reused by a second circuit in the first circuitry unit, or by a third circuit in a second circuitry unit at a different time.

Embodiments thus may be implemented in hardware (e.g., circuitry), firmware, software, or any combination thereof. Embodiments may also be implemented as instructions stored on a machine-readable medium, which may be read and executed by one or more processors. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

The various components described herein may be referred to as "modules," "units," "devices", "functionality", or similar terms. Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such components, as applicable and relevant, may alternatively be referred to herein as "circuitry," "controllers," "processors," or "processing circuitry," or using alternative terms as noted herein.

Additional aspects and features of the present disclosure are set forth in the following numbered examples:

Example 1 is a method of generating a computed cephalometric image, comprising: obtaining panoramic image data produced from a panoramic x-ray scan; generating a representation of the panoramic image data in a defined three-dimensional space; determining a geometry of a cephalometric view in the defined three-dimensional space; modeling simulated x-rays in the geometry of the cephalometric view to identify portions of the panoramic image data to be used in the computed cephalometric image; and outputting the computed cephalometric image.

In Example 2, the subject matter of Example 1 optionally includes subject matter where the panoramic image data comprises a two-dimensional panoramic image, and wherein the method further comprises reconstructing the two-dimensional panoramic image from a plurality of x-ray projection images.

In Example 3, the subject matter of Example 2 optionally includes subject matter where the plurality of x-ray projection images is captured in an extraoral x-ray system with a full-frame panoramic (FFPAN) scan, and wherein the method further comprises performing at least one image correction technique on the plurality of x-ray projection images or the two-dimensional panoramic image.

In Example 4, the subject matter of any one or more of Examples 2-3 optionally include subject matter where reconstructing the two-dimensional panoramic image from the plurality of x-ray projection images comprises extending a focal layer thickness of a focal layer, wherein extending the focal layer thickness includes at least one of: omitting respective frames of the plurality of x-ray projection images for use in reconstructing the two-dimensional panoramic image; or using a weighted collimator beam profile of at least one projection image of the plurality of x-ray projection images used in reconstructing the two-dimensional panoramic image.

In Example 5, the subject matter of any one or more of Examples 2-4 optionally include subject matter where reconstructing the two-dimensional panoramic image comprises combining two height-shifted projection images to create the two-dimensional panoramic image with an expanded image height.

In Example 6, the subject matter of any one or more of Examples 1-5 optionally include subject matter where generating the representation of the panoramic image data in the defined three-dimensional space comprises mapping pixel data of a two-dimensional panoramic image to voxels of a three-dimensional mesh in the defined three-dimensional space, and wherein the three-dimensional mesh corresponds to a focal curve of the two-dimensional panoramic image in a geometry of the panoramic x-ray scan.

In Example 7, the subject matter of Example 6 optionally includes subject matter where modeling the simulated x-rays comprises intersecting the simulated x-rays in the defined three-dimensional space through the voxels of the three-dimensional mesh, and wherein the method further comprises: creating a plurality of virtual cephalometric projection images from the voxels of the three-dimensional mesh; and reconstructing the computed cephalometric image from the plurality of virtual cephalometric projection images.

In Example 8, the subject matter of Example 7 optionally includes weighing image information of duplicated points in the plurality of virtual cephalometric projection images.

In Example 9, the subject matter of any one or more of Examples 6-8 optionally include subject matter where modeling the simulated x-rays comprises intersecting the simulated x-rays in the defined three-dimensional space through the voxels of the three-dimensional mesh to a virtual cephalometric image, and wherein the method further comprises: modeling one x-ray beam per pixel of the virtual cephalometric image; and creating the computed cephalometric image from pixels of the virtual cephalometric image.

In Example 10, the subject matter of Example 9 optionally includes weighing image information of duplicated points along a same x-ray beam corresponding to a pixel in the virtual cephalometric image.

In Example 11, the subject matter of any one or more of Examples 1-10 optionally include subject matter where the simulated x-rays correspond to at least one virtual focus position originating from a virtual focus layer, and wherein the virtual focus layer corresponds to a simulated x-ray source in the geometry of the cephalometric view.

In Example 12, the subject matter of Example 11 optionally includes subject matter where the simulated x-rays extend in the defined three-dimensional space from the virtual focus layer, through a three-dimensional modeling of the panoramic image data, to a virtual projection image or a virtual cephalometric image constructed at a generated layer.

In Example 13, the subject matter of Example 12 optionally includes subject matter where respective distances in the defined three-dimensional space among the virtual focus layer, the three-dimensional modeling of the panoramic image data, and the generated layer are based on geometrical relationships used for cephalometric imaging.

In Example 14, the subject matter of any one or more of Examples 1-13 optionally include performing image post-processing on the computed cephalometric image.

Example 15 is at least one machine-readable medium, including instructions, which when executed by processing circuitry, cause the processing circuitry to perform any of the methods of Examples 1 to 14 to generate a computed cephalometric image from panoramic image data.

Example 16 is an x-ray system, comprising: an x-ray source and an x-ray detector for acquiring panoramic image data; and a computing unit for performing the any of the methods of Examples 1 to 14 to generate a computed cephalometric image from the panoramic image data.

Example 17 is a computer system, comprising: memory storing panoramic image data; and at least one processor configured to perform any of the methods of Examples 1 to 14 to generate a computed cephalometric image from the panoramic image data.

Example 18 is at least one non-transitory machine-readable medium, including instructions, which when executed by a computing system, cause the computing system to generate a computed cephalometric image from panoramic image data, by performing operations comprising: obtaining panoramic image data produced from a panoramic x-ray scan; generating a representation of the panoramic image data in a defined three-dimensional space; determining a geometry of a cephalometric view in the defined three-dimensional space; modeling simulated x-rays in the geometry of the cephalometric view to identify portions of the panoramic image data to be used in the computed cephalometric image; and outputting the computed cephalometric image.

In Example 19, the subject matter of Example 18 optionally includes subject matter where the panoramic image data comprises a two-dimensional panoramic image, and wherein the operations further comprise reconstructing the two-dimensional panoramic image from a plurality of x-ray projection images.

In Example 20, the subject matter of Example 19 optionally includes subject matter where the plurality of x-ray projection images is captured in an extraoral x-ray system with a full-frame panoramic (FFPAN) scan, and wherein the operations further comprise performing at least one image correction technique on the plurality of x-ray projection images or the two-dimensional panoramic image.

In Example 21, the subject matter of any one or more of Examples 19-20 optionally include subject matter where reconstructing the two-dimensional panoramic image from the plurality of x-ray projection images comprises extending a focal layer thickness of a focal layer, wherein extending the focal layer thickness includes at least one of: omitting respective frames of the plurality of x-ray projection images for use in reconstructing the two-dimensional panoramic image; or using a weighted collimator beam profile of at least one projection image of the plurality of x-ray projection images used in reconstructing the two-dimensional panoramic image.

In Example 22, the subject matter of any one or more of Examples 19-21 optionally include subject matter where reconstructing the two-dimensional panoramic image comprises combining two height-shifted projection images to create the two-dimensional panoramic image with an expanded image height.

In Example 23, the subject matter of any one or more of Examples 18-22 optionally include subject matter where generating the representation of the panoramic image data in the defined three-dimensional space comprises mapping pixel data of a two-dimensional panoramic image to voxels of a three-dimensional mesh in the defined three-dimensional space, and wherein the three-dimensional mesh corresponds to a focal curve of the two-dimensional panoramic image in a geometry of the panoramic x-ray scan.

In Example 24, the subject matter of Example 23 optionally includes subject matter where modeling the simulated x-rays comprises intersecting the simulated x-rays in the defined three-dimensional space through the voxels of the three-dimensional mesh, and wherein the operations further comprise: creating a plurality of virtual cephalometric projection images from the voxels of the three-dimensional mesh; and reconstructing the computed cephalometric image from the plurality of virtual cephalometric projection images.

In Example 25, the subject matter of Example 24 optionally includes subject matter where the operations further comprise weighing image information of duplicated points in the plurality of virtual cephalometric projection images.

In Example 26, the subject matter of any one or more of Examples 23-25 optionally include subject matter where modeling the simulated x-rays comprises intersecting the simulated x-rays in the defined three-dimensional space through the voxels of the three-dimensional mesh to a virtual cephalometric image, and wherein the operations further comprise: modeling one x-ray beam per pixel of the virtual cephalometric image; and creating the computed cephalometric image from pixels of the virtual cephalometric image.

In Example 27, the subject matter of Example 26 optionally includes subject matter where the operations further comprise: weighing image information of duplicated points along a same x-ray beam corresponding to a pixel in the virtual cephalometric image.

In Example 28, the subject matter of any one or more of Examples 18-27 optionally include subject matter where the simulated x-rays correspond to at least one virtual focus position originating from a virtual focus layer, and wherein the virtual focus layer corresponds to a simulated x-ray source in the geometry of the cephalometric view.

In Example 29, the subject matter of Example 28 optionally includes subject matter where the simulated x-rays extend in the defined three-dimensional space from the virtual focus layer, through a three-dimensional modeling of the panoramic image data, to a virtual projection image or a virtual cephalometric image constructed at a generated layer.

In Example 30, the subject matter of Example 29 optionally includes subject matter where respective distances in the defined three-dimensional space among the virtual focus layer, the three-dimensional modeling of the panoramic image data, and the generated layer are based on geometrical relationships used for cephalometric imaging.

In Example 31, the subject matter of any one or more of Examples 18-30 optionally include subject matter where the operations further comprise performing image post-processing on the computed cephalometric image.

Example 32 is a computer system, comprising: processing circuitry; and a memory device including instructions embodied thereon, wherein the instructions, which when executed by the processing circuitry, configure the processing circuitry to generate a computed cephalometric image from panoramic image data, with operations to: obtain panoramic image data produced from a panoramic x-ray scan; generate a representation of the panoramic image data in a defined three-dimensional space; determine a geometry of a cephalometric view in the defined three-dimensional space; model simulated x-rays in the geometry of the cephalometric view to identify portions of the panoramic image data to be used in the computed cephalometric image; and output the computed cephalometric image.

In Example 33, the subject matter of Example 32 optionally includes subject matter where the panoramic image data comprises a two-dimensional panoramic image, and wherein the operations further include to reconstruct the two-dimensional panoramic image from a plurality of x-ray projection images.

In Example 34, the subject matter of Example 33 optionally includes subject matter where the plurality of x-ray projection images is captured in an extraoral x-ray system with a full-frame panoramic (FFPAN) scan, and wherein the operations further include to perform at least one image correction technique on the plurality of x-ray projection images or the two-dimensional panoramic image.

In Example 35, the subject matter of any one or more of Examples 33-34 optionally include subject matter where to reconstruct the two-dimensional panoramic image from the plurality of x-ray projection images includes operations to extend a focal layer thickness of a focal layer, wherein to extend the focal layer thickness includes at least one of: omitting respective frames of the plurality of x-ray projection images for use in reconstructing the two-dimensional panoramic image; or using a weighted collimator beam profile of at least one projection image of the plurality of x-ray projection images used in reconstructing the two-dimensional panoramic image.

In Example 36, the subject matter of any one or more of Examples 33-35 optionally include subject matter where to reconstruct the two-dimensional panoramic image includes operations to combine two height-shifted projection images to create the two-dimensional panoramic image with an expanded image height.

In Example 37, the subject matter of any one or more of Examples 32-36 optionally include subject matter where to generate the representation of the panoramic image data in the defined three-dimensional space includes operations to map pixel data of a two-dimensional panoramic image to voxels of a three-dimensional mesh in the defined three-dimensional space, and wherein the three-dimensional mesh corresponds to a focal curve of the two-dimensional panoramic image in a geometry of the panoramic x-ray scan.

In Example 38, the subject matter of Example 37 optionally includes subject matter where to model the simulated x-rays includes operations to intersect the simulated x-rays in the defined three-dimensional space through the voxels of the three-dimensional mesh, and wherein the operations further include to: create a plurality of virtual cephalometric projection images from the voxels of the three-dimensional mesh; and reconstruct the computed cephalometric image from the plurality of virtual cephalometric projection images.

In Example 39, the subject matter of Example 38 optionally includes subject matter where the operations further include to weigh image information of duplicated points in the plurality of virtual cephalometric projection images.

In Example 40, the subject matter of any one or more of Examples 37-39 optionally include subject matter where to model the simulated x-rays includes operations to intersect the simulated x-rays in the defined three-dimensional space through the voxels of the three-dimensional mesh to a virtual cephalometric image, and wherein the operations further include to: model one x-ray beam per pixel of the virtual cephalometric image; and create the computed cephalometric image from pixels of the virtual cephalometric image.

In Example 41, the subject matter of Example 40 optionally includes the operations further include to: weigh image information of duplicated points along a same x-ray beam corresponding to a pixel in the virtual cephalometric image.

In Example 42, the subject matter of any one or more of Examples 32-41 optionally include subject matter where the simulated x-rays correspond to at least one virtual focus position originating from a virtual focus layer, and wherein the virtual focus layer corresponds to a simulated x-ray source in the geometry of the cephalometric view.

In Example 43, the subject matter of Example 42 optionally includes subject matter where the simulated x-rays extend in the defined three-dimensional space from the virtual focus layer, through a three-dimensional modeling of the panoramic image data, to a virtual projection image or a virtual cephalometric image constructed at a generated layer.

In Example 44, the subject matter of Example 43 optionally includes subject matter where respective distances in the defined three-dimensional space among the virtual focus layer, the three-dimensional modeling of the panoramic image data, and the generated layer are based on geometrical relationships used for cephalometric imaging.

In Example 45, the subject matter of any one or more of Examples 32-44 optionally include subject matter where the operations further include to perform image post-processing on the computed cephalometric image.

The various embodiments described above have been presented by way of example and not limitation. It will be apparent to persons skilled in the relevant art(s) that various changes in form and detail can be made therein (e.g., different hardware, communications protocols, and the like) without departing from the scope of the present embodiments. In addition, it should be understood that the attached drawings, which highlight functionality described herein, are presented as illustrative examples. The architecture of the present aspects is sufficiently flexible and configurable, such that it can be utilized and navigated in ways other than that shown in the drawings.

What is claimed is:

1. A method of generating a computed cephalometric image, comprising:

obtaining panoramic image data produced from a panoramic x-ray scan;

generating a representation of the panoramic image data in a defined three-dimensional space;

determining a geometry of a cephalometric view in the defined three-dimensional space;

modeling simulated x-rays in the geometry of the cephalometric view to identify portions of the panoramic image data to be used in the computed cephalometric image; and outputting the computed cephalometric image.

2. The method of claim 1, wherein the panoramic image data comprises a two-dimensional panoramic image, and wherein the method further comprises reconstructing the two-dimensional panoramic image from a plurality of x-ray projection images.

3. The method of claim 2, wherein the plurality of x-ray projection images is captured in an extraoral x-ray system with a full-frame panoramic (FFPAN) scan, and wherein the method further comprises performing at least one image correction technique on the plurality of x-ray projection images or the two-dimensional panoramic image.

4. The method of claim 2, wherein reconstructing the two-dimensional panoramic image from the plurality of x-ray projection images comprises extending a focal layer thickness of a focal layer, wherein extending the focal layer thickness includes at least one of:

omitting respective frames of the plurality of x-ray projection images for use in reconstructing the two-dimensional panoramic image; or using a weighted collimator beam profile of at least one projection image of the plurality of x-ray projection images used in reconstructing the two-dimensional panoramic image.

5. The method of claim 2, wherein reconstructing the two-dimensional panoramic image comprises combining two height-shifted projection images to create the two-dimensional panoramic image with an expanded image height.

6. The method of claim 1, wherein generating the representation of the panoramic image data in the defined three-dimensional space comprises mapping pixel data of a two-dimensional panoramic image to voxels of a three-dimensional mesh in the defined three-dimensional space, and wherein the three-dimensional mesh corresponds to a focal curve of the two-dimensional panoramic image in a geometry of the panoramic x-ray scan.

7. The method of claim 6, wherein modeling the simulated x-rays comprises intersecting the simulated x-rays in the defined three-dimensional space through the voxels of the three-dimensional mesh, and wherein the method further comprises:

creating a plurality of virtual cephalometric projection images from the voxels of the three-dimensional mesh; and reconstructing the computed cephalometric image from the plurality of virtual cephalometric projection images.

8. The method of claim 7, further comprising:

weighing image information of duplicated points in the plurality of virtual cephalometric projection images.

9. The method of claim 6, wherein modeling the simulated x-rays comprises intersecting the simulated x-rays in the defined three-dimensional space through the voxels of the three-dimensional mesh to a virtual cephalometric image, and wherein the method further comprises:

modeling one x-ray beam per pixel of the virtual cephalometric image; and creating the computed cephalometric image from pixels of the virtual cephalometric image.

10. The method of claim 9, further comprising:

weighing image information of duplicated points along a same x-ray beam corresponding to a pixel in the virtual cephalometric image.

11. The method of claim 1, wherein the simulated x-rays correspond to at least one virtual focus position originating from a virtual focus layer, and wherein the virtual focus layer corresponds to a simulated x-ray source in the geometry of the cephalometric view.

12. The method of claim 11, wherein the simulated x-rays extend in the defined three-dimensional space from the virtual focus layer, through a three-dimensional modeling of the panoramic image data, to a virtual projection image or a virtual cephalometric image constructed at a generated layer.

13. The method of claim 12, wherein respective distances in the defined three-dimensional space among the virtual focus layer, the three-dimensional modeling of the panoramic image data, and the generated layer are based on geometrical relationships used for cephalometric imaging.

14. The method of claim 1, further comprising:

performing image post-processing on the computed cephalometric image.

15. At least one non-transitory machine-readable medium, including instructions, which when executed by a computing system, cause the computing system to generate a computed cephalometric image from panoramic image data, by performing operations comprising:

obtaining panoramic image data produced from a panoramic x-ray scan;

generating a representation of the panoramic image data in a defined three-dimensional space;

determining a geometry of a cephalometric view in the defined three-dimensional space;

modeling simulated x-rays in the geometry of the cephalometric view to identify portions of the panoramic image data to be used in the computed cephalometric image; and outputting the computed cephalometric image.

16. The at least one non-transitory machine-readable medium of claim 15, wherein the panoramic image data comprises a two-dimensional panoramic image, and wherein the operations further comprise reconstructing the two-dimensional panoramic image from a plurality of x-ray projection images.

17. The at least one non-transitory machine-readable medium of claim 16, wherein the plurality of x-ray projection images is captured in an extraoral x-ray system with a full-frame panoramic (FFPAN) scan.

18. An x-ray system, comprising:

an x-ray source and an x-ray detector for acquiring panoramic image data; and a computing unit comprising processing circuitry and a memory device including instructions embodied thereon, wherein the instructions, which when executed by the processing circuitry, configure the processing circuitry to generate a computed cephalometric image from panoramic image data, with operations to:

generate a representation of the panoramic image data in a defined three-dimensional space;

determine a geometry of a cephalometric view in the defined three-dimensional space;

model simulated x-rays in the geometry of the cephalometric view to identify portions of the panoramic image data to be used in the computed cephalometric image; and output the computed cephalometric image.

19. The x-ray system of claim 18, wherein the panoramic image data comprises a two-dimensional panoramic image, and wherein the operations further comprise reconstructing the two-dimensional panoramic image from a plurality of x-ray projection images.

20. The x-ray system of claim 19, wherein the plurality of x-ray projection images is captured in an extraoral x-ray system with a full-frame panoramic (FFPAN) scan.

* * * * *